(12) United States Patent
Flick

(10) Patent No.: US 10,086,144 B2
(45) Date of Patent: Oct. 2, 2018

(54) SYRINGE BARREL

(71) Applicant: Conrad Flick, Bettendorf, IA (US)

(72) Inventor: Conrad Flick, Bettendorf, IA (US)

( * ) Notice: Subject to any disclaimer, the term of this patent is extended or adjusted under 35 U.S.C. 154(b) by 38 days.

(21) Appl. No.: 14/281,612

(22) Filed: May 19, 2014

(65) Prior Publication Data
US 2015/0328407 A1 Nov. 19, 2015

(51) Int. Cl.
*A61M 5/31* (2006.01)
*A61M 5/315* (2006.01)
*A61M 5/34* (2006.01)

(52) U.S. Cl.
CPC ........ *A61M 5/3148* (2013.01); *A61M 5/3135* (2013.01); *A61M 5/3134* (2013.01); *A61M 5/31511* (2013.01); *A61M 5/31515* (2013.01); *A61M 5/347* (2013.01); *A61M 5/348* (2013.01); *A61M 2005/3112* (2013.01); *A61M 2005/3131* (2013.01); *A61M 2005/31521* (2013.01); *A61M 2005/342* (2013.01); *A61M 2205/583* (2013.01); *A61M 2205/586* (2013.01)

(58) Field of Classification Search
CPC .. A61M 2005/3112; A61M 2005/3246; A61M 5/3137; A61M 5/3148; A61M 5/148; A61M 5/152; A61M 5/2425
See application file for complete search history.

(56) References Cited

U.S. PATENT DOCUMENTS

| 2,725,057 | A | * | 11/1955 | Lockhart | ............... A61M 5/282 604/193 |
| 4,772,267 | A | * | 9/1988 | Brown | ............. A61M 25/0693 604/168.01 |
| 5,037,393 | A | * | 8/1991 | Ellgass | ................. A61M 5/348 604/110 |
| 2003/0097096 | A1 | * | 5/2003 | Niedospial, Jr. | ..... A61M 5/3129 604/218 |
| 2009/0198194 | A1 | * | 8/2009 | Madin | ................. A61M 5/3148 604/218 |

* cited by examiner

*Primary Examiner* — Imani Hayman
*Assistant Examiner* — James D Ponton
(74) *Attorney, Agent, or Firm* — Brad Kile; Scott Houtteman

(57) ABSTRACT

A syringe barrel including a tubular, barrel body operable to receive a syringe plunger at a proximal end thereof and a syringe needle at a distal end and sidewalls of said syringe body being flexible and elliptical in cross-section and opposing compression of said syringe barrel at opposite ends a major axis of said syringe barrel cross-section serving to operably flex the elliptical cross-section of said syringe body into a more circular cross-sectional configuration and increasing the volume of said syringe barrel body and concomitantly serving to create a relative vacuum within said syringe body as compared with the configuration of said syringe tubular, barrel body prior to application of said compression.

6 Claims, 6 Drawing Sheets

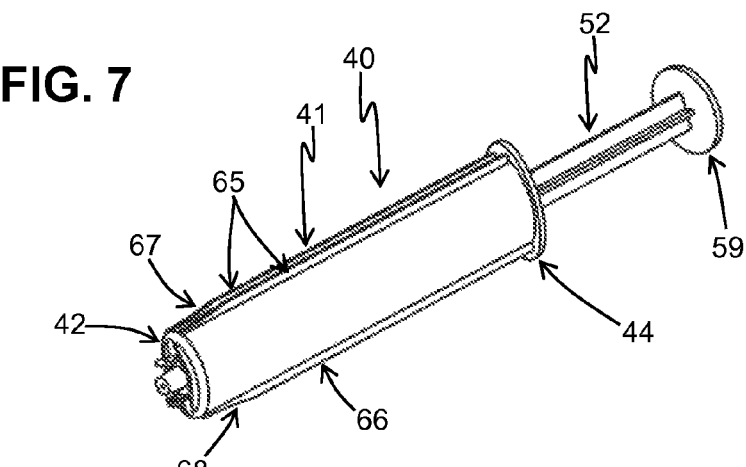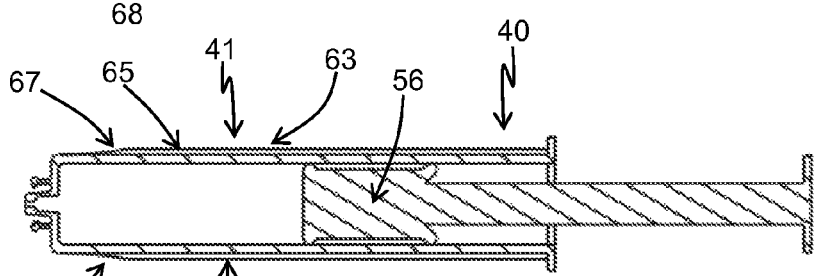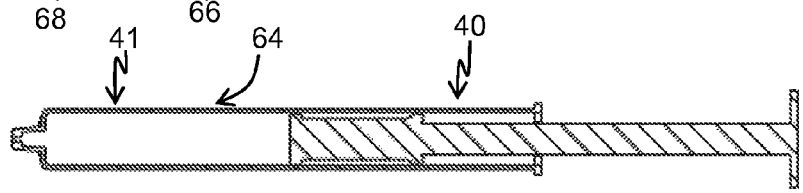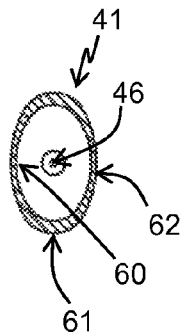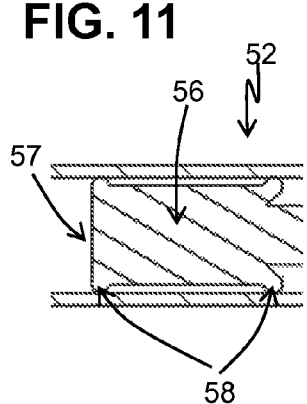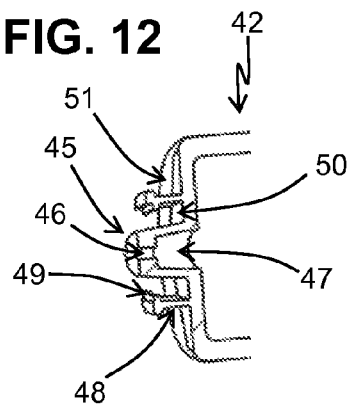

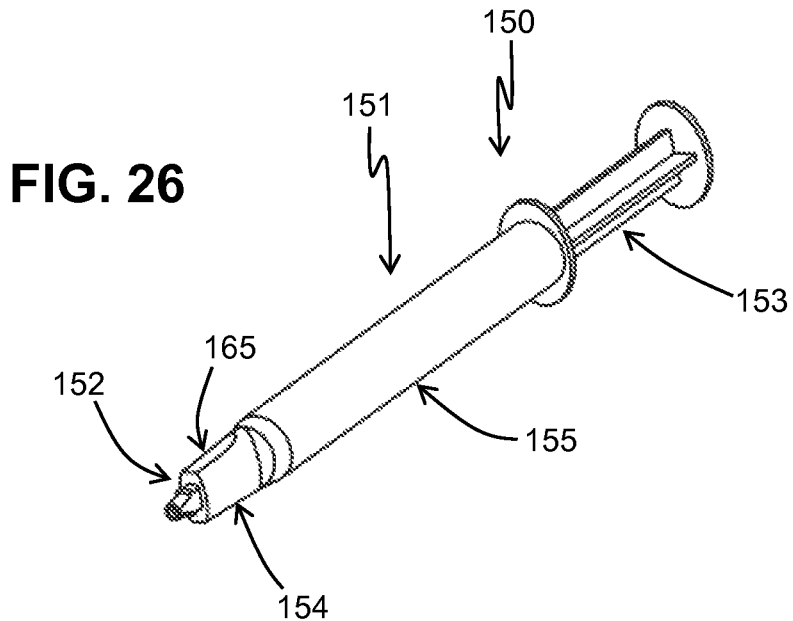
FIG. 26
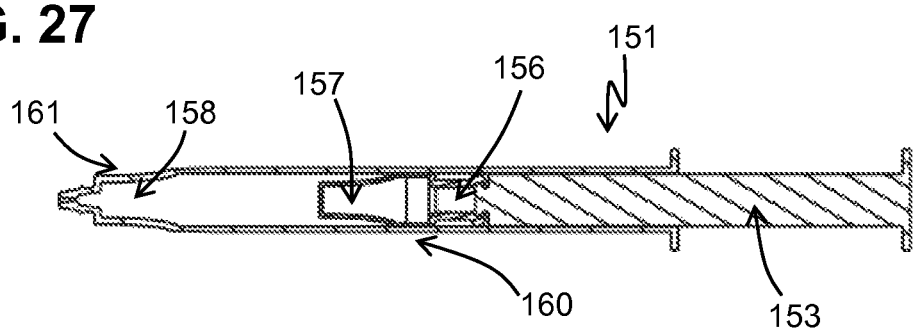
FIG. 27
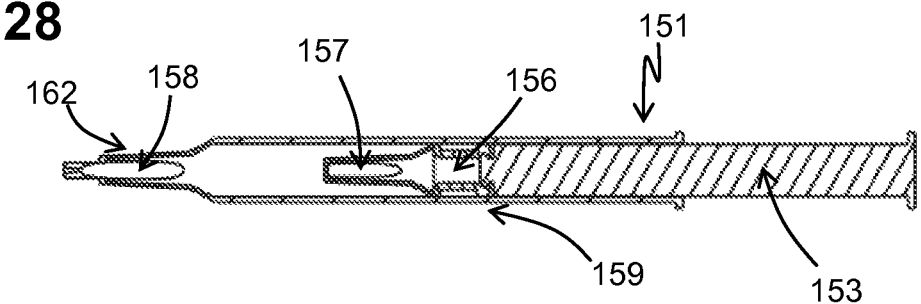
FIG. 28
FIG. 29
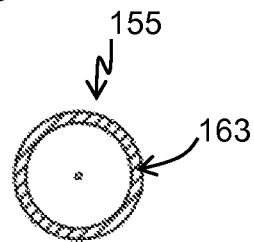
FIG. 30
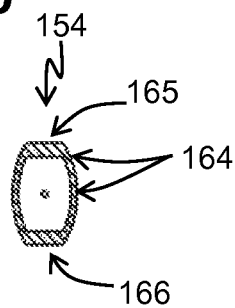

SYRINGE BARREL

BACKGROUND OF THE INVENTION

Field of the Invention

The present invention relates to a syringe device for safely and facilely administering a fluid injectant into a patient. More particular, the invention relates to certain improvements for single-use syringes for injecting liquids or gels with selective aspirating capabilities. The syringe device can be economically molded from a single material and can be similar in appearance to a common syringe and easily adaptable to the current administering techniques. The syringe, when injecting, can be disposed in a natural hand-held position to minimize movement insuring the same sampling and injection site.

The use of conventional syringes for patient injections is known. A syringe device typically comprises: a rigid, circular cylindrical barrel defining a fluid retaining chamber with an open proximal end and a distal wall having a central frustum having a fluid passageway communicating the barrel with an attached distally extending cannula. A plunger extends proximally from of the barrel and with a distal stopper in a fluid-tight engagement within the barrel.

When it is necessary to know needle placement relative to a patient's vascular system, aspiration is necessary. To aspirate, the volume of the syringe barrel is expanded to create a vacuum and ultimately draw bodily fluid into the neck of the syringe to determine if a blood vessel has been penetrated. This may be done actively or passively.

Active aspiration is typically performed by manually retracting a syringe plunger from within the syringe barrel after inserting a sharp cannula into the patient to obtain an observable body fluid sample in the neck of the syringe barrel. This can be a two handed awkward process. Another active aspirating method is to retract the plunger seal's leading face by withdrawing an attached central shaft within the plunger to create a vacuum within the syringe barrel chamber to aspirate body fluids into the barrel to detect the possible presence of blood in the sample. Another process utilizes a hand apparatus enclosing the syringe which mechanically retracts or extends the plunger to aspirate or inject.

Other types of syringe bodies offer passive aspiration. In one example, a plunger is momentarily depressed into the syringe barrel expanding a pliable, sealing member prior to placing the needle stick. After the needle is inserted into a patient the plunger is released allowing the sealing member to retract and reestablish an initial configuration. This creates a vacuum to draw up bodily fluids into barrel neck for checking needle placement. A major drawback with this process is the awkwardness of depressing the plunger and maintaining the expanded sealing member prior to and during the needle stick. Another passive version uses a momentary syringe barrel, sidewall compression prior to inserting the needle into the patient. When released, the barrel volume returns to initial shape drawing in bodily fluid. This also has a degree of awkwardness associated with maintaining a consistent barrel compression during the needle stick. Both examples can expel a random amount of injectant prior to needle placement making dosages uncertain.

This invention relates to transitioning syringe barrel and plunger configurations after needle placement. A circular barrel cross-section provides the largest internal volume for a given barrel circumference or perimeter. Any distortion of a non-circular or non-regular polygonal cross-section to achieve a circular or regular polygonal cross-section will increase the section's area and ultimately its respective volume for a given barrel length. The barrel volume referred to is the actual fluid volume established by the plunger seal position within the barrel. This distortion may result in circular, elliptical, or linear sidewalls or a combination configuration. This sidewall flexibility is achieved either with wall thickness, thickness variations, a compliment of living hinges, or a combination thereof. The overall shape of the syringe body may be cylindrical or conical for an elliptical cross-section, or planar for a regular polygonal cross-section.

A distortion of a molded configuration may be achieved through folding, stretching, and/or squeezing the syringe barrel. There is a pressure differential between a gripping pressure required to place a needle into a patient and the pressure required to aspirate fluid from the patient. This prevents inadvertent aspiration prior to the needle stick possibly drawing air into the syringe.

In one embodiment, the syringe body sidewall is elliptical in cross-section. The wall thickness may be constant or could vary from the opposing, circular, structural portions capping the major axis to the opposing, gradually thinning, yieldable elliptical ones capping the minor axis. The gradual thinning sidewalls produce a more predictable barrel volume increase by encouraging the elliptical section center to move outward initially. The technique is to squeeze the barrel's circular sections after the needle stick to transition its elliptical cross-section towards a circular cross-section increasing the section's respective area and the barrel's overall volume for a given plunger-seal position.

Another embodiment uses planar sidewalls forming a parallelogram with uneven diagonals. These sidewalls may have a uniform structural thickness with living hinges at their junctures; together, when depressed, allow the shape to transition towards a square increasing the body's volume. This thickness needs to be sufficient for gripping and needle placement without body deformation, but yieldable when the living hinges capping the longest diagonal are depressed when aspiration is desired.

The frustum of the barrel's distal wall may have a stepped interior volume to provide a smaller volume, viewing window permitting a smaller, concentrated fluid sampling. This window may be visible behind a partial luer-lock coupler if one is present.

This invention provides a syringe which may be selectively aspirated single-handedly, without altering one's grip, after the needle is inserted into a patient during an injection.

The difficulties and limitations suggested in the preceding and desired features are not intended to be exhaustive but rather are among many which may tend to reduce the effectiveness and user satisfaction with previously known syringes. Other noteworthy problems and limitations may also exist; however, those presented above should be sufficient to demonstrate that syringes appearing in the past will admit to worthwhile improvement.

BRIEF SUMMARY

One preferred embodiment of the invention which is intended to address concerns and accomplish at least some of the foregoing objects comprises a syringe capable of being selectively molded from a single material. This embodiment resembles a typical syringe in appearance, except with an elliptical instead of a circular cross-sectional body. This unique body is sufficiently rigid for gripping, yet flexible enough to be reshaped allowing a user to selectively aspirate for determining proper needle placement without changing hand positioning before completing an injection. A typical grip would be to hold the syringe with one's thumb and middle finger on the pads capping the major axis of the distal wall or the actual syringe body in the region of the plunger seal, and depress the plunger with the index finger. Alternatively the syringe barrel may be grasped between the index and middle finger with an operator's thumb on the syringe plunger. To aspirate, one simply squeezes the elliptical body about the major axis transforming it towards a circular configuration after placing the needle. An aspirated, fluid sample is visible in a reduced diameter, neck portion at the barrel's distal end. This chamber's length with reduced volume requires less fluid for determining the aspirated fluids origin. The injection is completed by then depressing the plunger and properly disposing the spent syringe.

Stowing the syringe prior to disposal may be accomplished with any of the current techniques, such as recapping, flip enclosures for shielding the needle tip, retracting needles, and others. Any needle attachment means may be used, such as insertion with adhesive or a luer lock coupler arrangement. The sealing member of the plunger may be formed entirely of the same material as the body using a modified partial O-ring or inverted cup-shaped configuration; or from an elastomeric material, such as rubber or silicone, with resilient, sealing engagement bands. The latter is secured to the plunger shaft with a complementing groove to the periphery bead of the plunger base. The plunger may have webs or similar structure to center itself within the chamber of the body and an elliptical base which maintains the body's elliptical nature in the sealing region. On the body, there are graduated indicia to determine the volume in relation to the plunger seal's position within syringe body.

DRAWINGS

Other objects and advantages of the present invention will become apparent from the following detailed description of preferred embodiments thereof taken in conjunction with the accompanying drawings wherein:

FIG. 7 is another embodiment with a greater axes length differential;

FIG. 8 is a longitudinal cross-section, side view of FIG. 7;

FIG. 9 is a longitudinal cross-section, top view of FIG. 7;

FIG. 10 is a cross-section of the syringe barrel of FIG. 7;

FIG. 11 is a side cross-section of FIG. 7 with an alternative plunger sealing member;

FIG. 12 is a cross-section of the distal region of the syringe in FIG. 7;

FIG. 26 is an alternative blended embodiment;

FIG. 27 is a longitudinal side cross-section;

FIG. 28 is a longitudinal side cross-section;

FIG. 29 is a cross-section of the elliptic cylindrical body; and

FIG. 30 is a cross-section of the circular cylindrical body.

DETAILED DESCRIPTION

Figure 1:
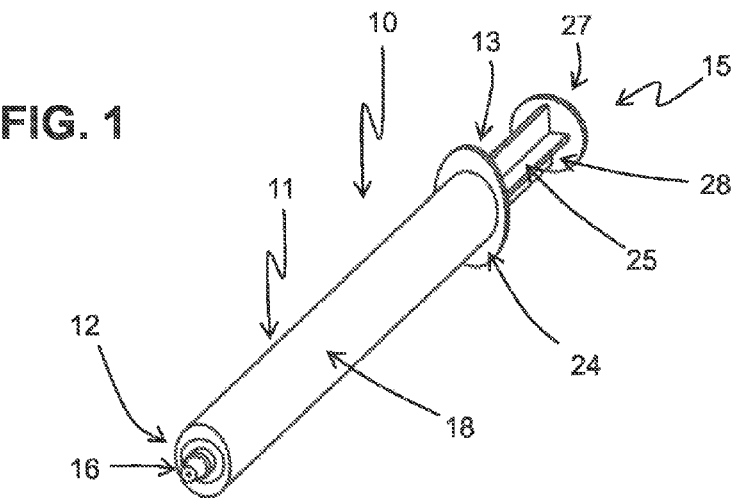
FIG. 1 is an axonometric view of a syringe in accordance with one embodiment of the invention.

Referring now particularly to the drawings, wherein like reference characters refer to like parts, and initially to FIG. 1, there will be seen an axonometric view of a syringe 10 in accordance with one preferred embodiment of the invention. The syringe 10 in FIG. 1 comprises a distally truncated, elliptic cylindrical barrel or body 11 and an axially sliding, sealing plunger 15. The barrel 11 has a uniform wall thickness 14 which provides a distinct difference between the gripping pressure needed to perform the needle stick and the compressive pressure needed for aspiration. This prevents an inadvertent aspiration prior to the needle stick. The distal end wall 12 has a frustum 16 possessing a stepped passageway 17 to provide fluid communication between a fluid chamber 18 of the barrel 11 and a needle. A retention ring 19 integrally surrounds the frustum 16 to selectively retain the needle cap with mating detent. At an open, proximal end 13 of barrel 11, a peripheral, gripping flange 24 maintains the elliptical nature of the barrel 11 and assists the holding of the syringe 10 during filling and administering an injection. The plunger 15 consists of a ribbed shaft 25 with distal and proximal ends, 26 and 27 respectively. A distal end 26 provides a slidable, cup seal 28 which is in fluid tight engagement with the sidewall 29 of fluid chamber 18. A 15's proximal end 27 of plunger 15 has a pressure pad 28 for finger placement to comfortably depress the plunger 15.

Figure 2:
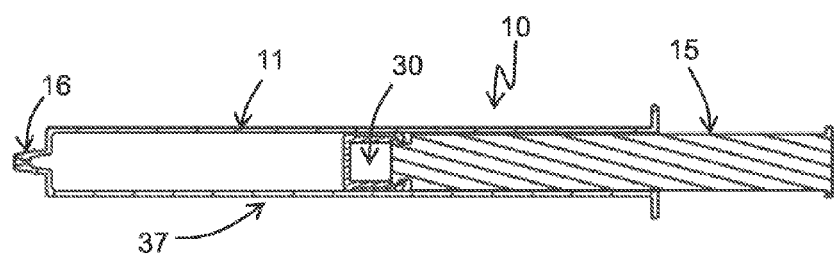
FIG. 2 is a longitudinal cross-section, side view of FIG. 1.
Figure 3:
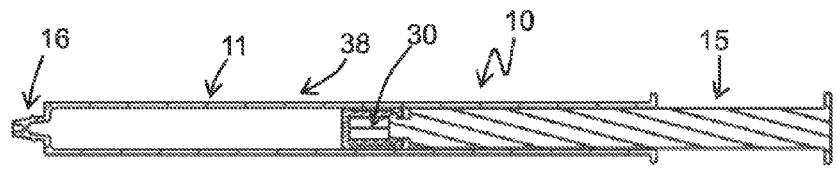
FIG. 3 is an additional longitudinal cross-section, top view of FIG. 1.

FIGS. 2 and 3 reveal side and top cross-sections of FIG. 1, respectively. Due to the elliptical nature of the barrel body 11, the profile 37 of the body in FIG. 2 is wider than the profile 38 in FIG. 3.

Figure 4:
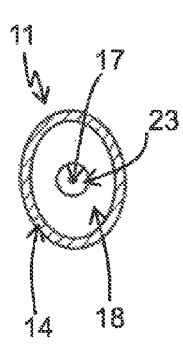
FIG. 4 is a cross-section of the syringe's elliptical body.

FIG. 4 is a cross-section of barrel body 11 revealing the elliptical sidewall 29 configuration of uniform thickness 14.

Figure 5:
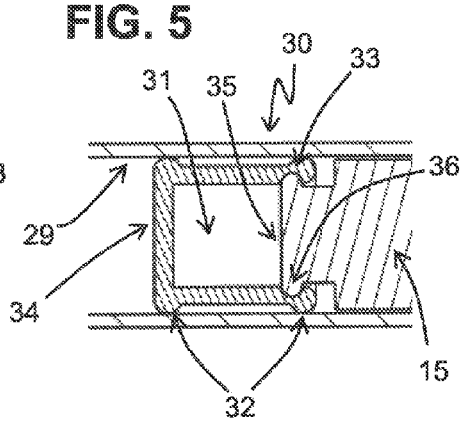
FIG. 5 is an enlarged view of a plunger's sealing member.

FIG. 5 is an enlarged view showing a sealing engagement of cup seal 30 with the sidewall 29. This fluid tight engagement is accomplished a hollowed, elastomeric cup-seal 30 with two sidewall 29 engaging bands 32, spaced apart to ensure axial travel the cup seal 30. The seal 30 is affixed to the plunger 15 about a beaded edge 36 on a distal base 35 of plunger 15 by a proximal peripheral groove 33. A hollowed interior 31 of the cup seal 30 permits a distal surface 34 to partially collapse when aspirating close to it, but resiliently reshapes to expel the injectant. The distal base 35 maintains the elliptical configuration of the barrel body 11 at the seal even when aspirating distortion is induced.

Figure 6:
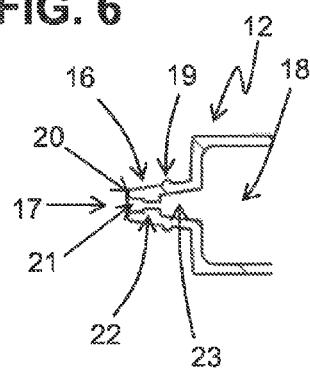
FIG. 6 is an enlarged view of the body's distal end.

FIG. 6 is an enlarged view showing the frustum 16 in greater detail. Within the frustum 16, the stepped passageway 17 has a flared distal opening 20 to accommodate adhesive to affix a needle in socket 21. The fluid passageway narrows forming a needle stop 22 before flaring again to form the viewing conical chamber 23 which allows the viewing of a smaller, concentrated sampling of the aspirated, fluid specimen prior to it entering the fluid chamber 18.

FIG. 7 is an axonometric view of another embodiment of a selectively aspirating syringe. Syringe 40 shares many similar features and their functionalities with syringe 10, such as a similar distally truncated, elliptic, cylindrical body 41 with gripping flange 44 and an axially sliding, ribbed plunger 52 with a distal seal 56 and a proximal finger pad 59. Two opposing, finger detents 67 and 68 on the distal end of aspirating rib sections 65 and 66, respectively, establish finger placement for holding the syringe. More distinguishing features of syringe 40 are revealed in detail in FIGS. 10-12.

FIGS. 8 and 9 display side and top sections, respectively, of FIG. 7. The profile 63 of body 41 in FIG. 8 is broader compared to the profile of body 41 in FIG. 9 due to its elliptical nature. FIG. 8 also displays finger detents 67 and 68 on the aspirating ribs 65 and 66. As explained earlier, these detents indicate proper finger placement for grasping the syringe body 41 to avoid inadvertent aspiration.

FIG. 10 is cross-section of an elliptical syringe barrel body 41. This illustrates a thickness variation of the sidewall 60 which promotes a predictable transition from an elliptical to a round configuration when the elliptical wall section 61 capping the major axis is depressed. This depression of wall section 61 causes a reduced radius in wall section 62 which caps the minor axis of the ellipse and transitions the elliptical body towards a circular shape which increases the section area and chamber volume.

FIG. 11 is an enlarged partial section of FIG. 8 which shows an integral plunger seal 56. The seal 56 of the plunger is a pair of O-rings 58 integrally molded onto a distal base 57 of the plunger, which when placed within the elliptical body 41 forms a fluid-tight engagement with sidewall 60 and maintains an axial travel seal. These O-rings 58 also assist in maintaining the elliptical nature of body 41 when a portion of the sidewall is depressed for aspiration. The surface contour of distal base 57 replicates the interior of distal end wall 42. This sealing means may have other forms: such as an applied O-ring instead of being integrally molded, or an outward, distal extension of the distal surface forming an inverted cup to serve as a wiper, or other slideable, sealing structure.

FIG. 12 is an enlarged view of distal wall features. The distal wall 42 has an extended, central frustum 45 and two opposing stanchions 48 which support a partial, luer thread 49 for needle attachment. The continuous pitch of the two partial sections of luer thread 49 draws a luer coupler of a needle sealingly onto frustum 45. The distal wall 42 surrounding the frustum varies in thickness for structural and yielding considerations. The thickened pads 50 support the luer thread stanchions 48 and provide gripping integrity for the needle stick, whereas the thinner panels 51 yield to assist in selective aspiration. The thinner yielding panels 51 distort during aspiration, but return to an initial configuration when the aspirating depression ceases and the actual injection occurs. Within the frustum 45, the passageway 46 expands proximally to form a viewing chamber 47. This permits viewing a smaller sampling of concentrated, aspirated fluid. The frustum hub 45 is of sufficient length to permit the viewing chamber 47 to be visible behind the luer coupler.

Figure 13:
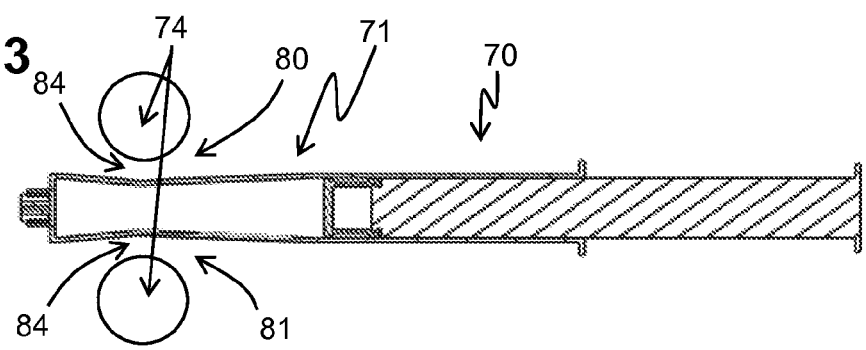
FIG. 13 is a side cross-section of FIG. 7 revealing an aspirated state.
Figure 14:
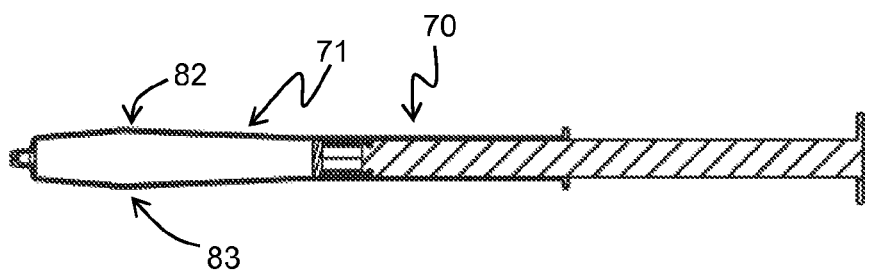
FIG. 14 is a top cross-section of FIG. 7 complimenting FIG. 13.

FIGS. 13 and 14 show an aspirating compression of another syringe embodiment 70 with similar body features 71 to syringe embodiment 40, and plunger 72 and distal wall 73 features similar to syringe embodiment 10. FIG. 13 is a side sectional view of syringe 70 showing fingers 74. Along curved walls 80 and 81 capping the major axis are points 84 of compression. The walls 82 and 83 capping the minor axis expand outwardly transitioning circularly during aspiration.

Figure 15:
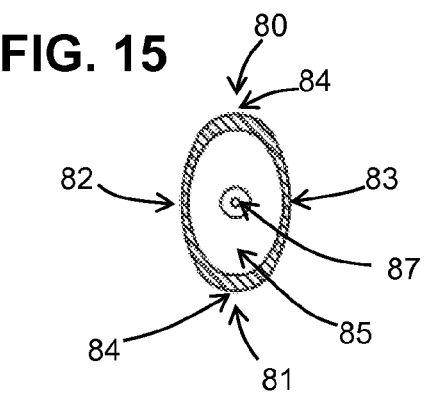
FIG. 15 is a cross-section of the syringe body prior to aspiration.
Figure 16:
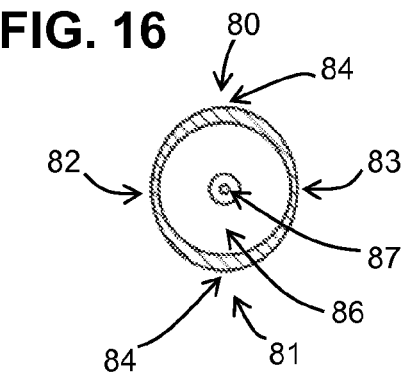
FIG. 16 is a cross-section of the syringe body during aspiration.

FIGS. 15 and 16 are cross sections of body 71 at the points of compression 84. FIG. 15 is prior to aspiration and FIG. 16 is at full aspiration. The varying wall thickness predictably transitions the body 71 uniformly from elliptical to circular. This shape transitioning creates a greater cross-sectional area from 85 to 86 resulting in a larger chamber volume which aspirates a sufficient specimen for viewing in the frustum window 87 to determine needle placement.

Figure 17:
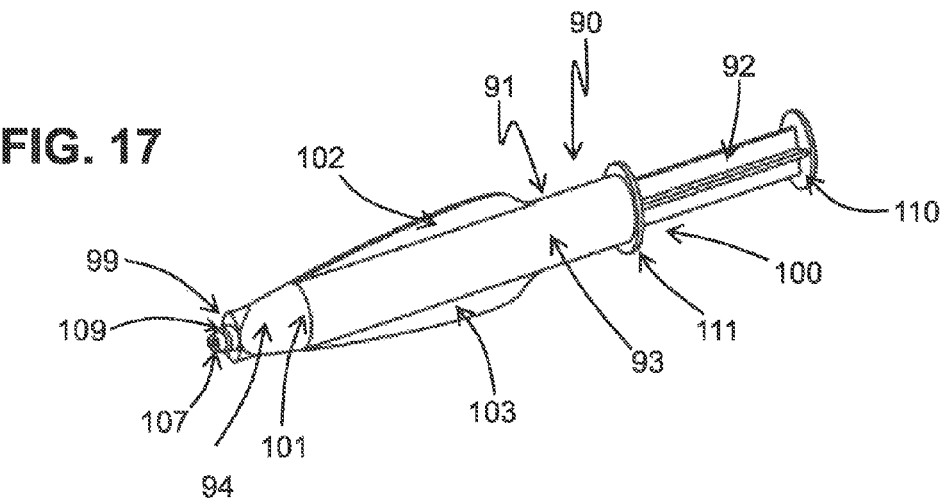
FIG. 17 is an additional embodiment utilizing a conical body.

FIG. 17 is an axonometric view of another syringe embodiment 90 with a body 91 being a combination of two differing shapes: an elliptic cylinder 93 joined to a truncated, elliptic cone 94. This structural configuration permits selective aspiration to occur along the entire length of the body 91 regardless of where the points of compression are made. This is useful when finger placement is removed from the distal wall due to accessibility of the injection site, for example, dental syringes.

The barrel body 91 consists of two central body portions, 93 and 94, a closed distal end 99, and an open proximal end 100. The juncture 101 of these two portions, 93 and 94, is smooth and continuous to assist an elliptical body 91 in circular transitioning. The proximal body portion 93 is an elliptical cylinder to provide the sliding seal 106 of plunger 92 with a common axial, cylindrical surface for a fluid tight engagement during travel. The distal portion 94 is an elliptic cone used to influence the entire sidewall portions 95 and 96, and 97 and 98 capping the major and minor axes, respectively, to hinge inwardly and outwardly, respectively, pivoting about their common distal end 99, when selective, aspirating compression occurs. The wall thickness thins from regions 95 and 96 to regions 97 and 98, respectively, to also assist transitioning. To assist in the uniform, hinged compressions of sidewalls 95 and 96, there are opposing, continuous ribs 102 and 103 with finger placement detents 104 and 105. As compression pressure is applied to finger detents 104 and 105, ribs 102 and 103 move inwardly transitioning body 91 into a circular section posture. The distal wall 99 and proximal opening 100 are similar in structure to embodiment 10. Wall 99 supports frustum 107 with stepped passageway 108 and cap retention ring 109. A peripheral, gripping flange 111 is formed about opening 100. The plunger 92 is structurally similar to previous versions with a ribbed shaft, finger pad 110, and an attachment means 115 to the elastomeric seal 106.

Figure 18:
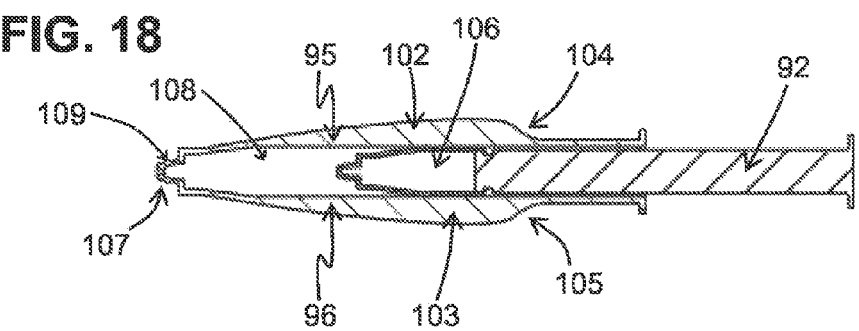
FIG. 18 is a side cross-section of FIG. 14.
Figure 19:
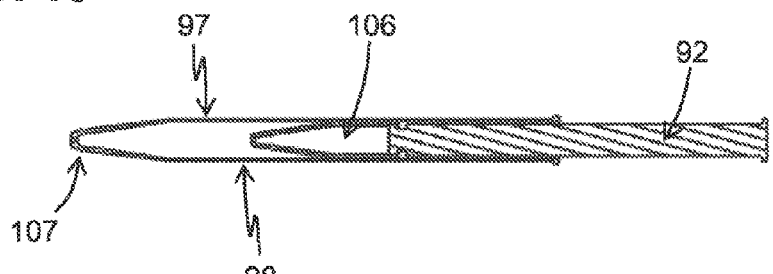
FIG. 19 is a top cross-section of FIG. 14.

FIGS. 18 and 19 are side and top sections of FIG. 17. These views illustrate the configuration of seal 106 and its relationship within the body 91. The seal 106 has two components which are shown in FIG. 21.

Figure 20:
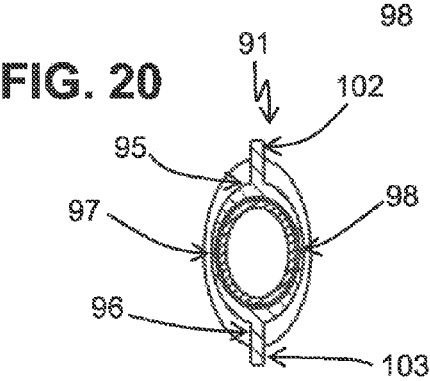
FIG. 20 is an enlarged cross-section of syringe body.

FIG. 20 represents a cross-section of the elliptical conical body 91. This view reveals thinning of the sidewalls from the major axis capping sections 95 and 96 to the minor axis capping sections 97 and 98. The ribs 102 and 103 sit atop the major axis.

Figure 21:
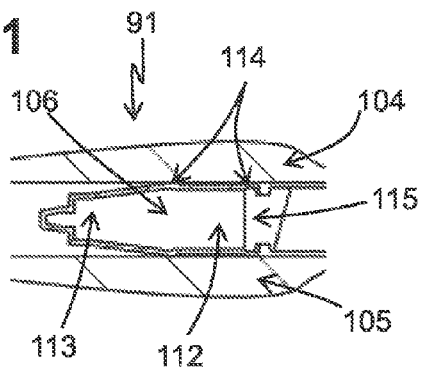
FIG. 21 is an enlarged view of FIG. 18 in the region of the plunge seal.

FIG. 21 is an enlarged portion of the side section of body 91 showing a seal configuration 106 and fluid tight relationship with body 91. Like the body 91, its proximal portion 112 is an elliptical cylinder and the distal portion 113 is a truncated elliptic cone. Cylindrical portion 112 has two spaced, integrally molded O-rings 114 for the fluid seal and to ensure axial travel within body 91. The hollow, elliptic cone 113 will partially collapse when aspirating compression is applied to finger detents 104 and 105 forcing ribs 102 and 103 inward.

Figure 22:
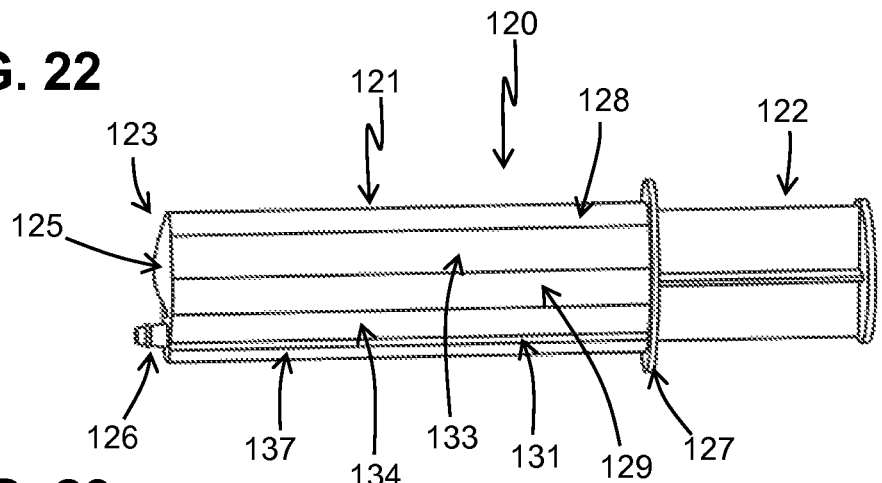
FIG. 22 is an alternative kite shaped embodiment.
Figure 25:
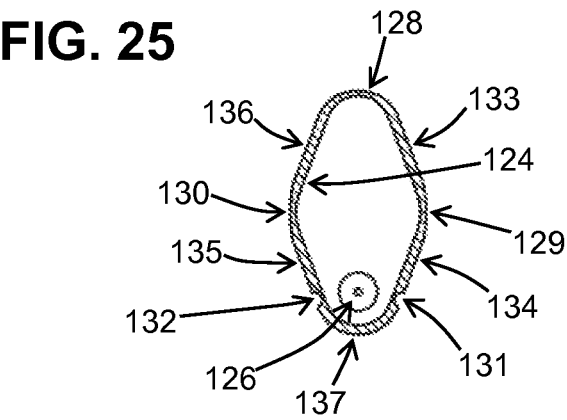
FIG. 25 is an enlarged cross-section of the syringe body.

FIGS. 22 and 25 are an axonometric view and a cross-sectional view, respectively, of polygonal syringe embodiment 120. A distinguishing feature is its "n-gon" cross-sectional shape, where "n" represents the number of sides. In this instance, body 121 is a modified kite shaped polygon. The polygon's vertices are replaced with living hinges 128, 129, and 130. These hinge sections are of sufficient interior, tangential radii to permit a fluid tight engagement of the plunger seal 134 and the interior sidewall's surfaces of body 121. The body panels 133, 134, 135, and 136 and living hinges 128, 129, 130, and 131 are of sufficient thickness to maintain the body's configuration and thinness to be yieldable allowing deformation for aspiration This thickness may be uniform throughout or have subtle variations expressed in the outer surface only, leaving a continuous inner surface 124 for a fluid tight arrangement with plunger seal 138.

Aspiration is performed by compressing body 121 about living hinge 128 and panel 137, shortening major diagonal and lengthening minor diagonal. As the two short sides of the kite shape become linear the cross sectional area increases. The kite body 121 transitions about living hinges 131 and 132 of base 137. Arcuate base 137 is of sufficient thickness to support frustum 126 in distal wall 123 minimizing movement. In this embodiment, body panels 133, 134, 135, and 136 are planar, but could be slightly arcuate. The frustum 126 of the distal wall 123 is no longer central but moved towards base panel 137 to allow the temporary flattening of central panel 125 during aspiration. The thickness of panel 125 reestablishes its shape once aspiration is complete. This movement of frustum 126 permits a partial luer thread coupler to be attached below panel 137 for single axis molding.

In this embodiment the frustum 126 on the distal wall 123 and the plunger configuration 122 and seal attachment means 142 directly references syringe 10. However, a complete or partial luer coupler feature or any needle attachment means along with any fluid tight seal arrangement could replace one or both.

Figure 23:
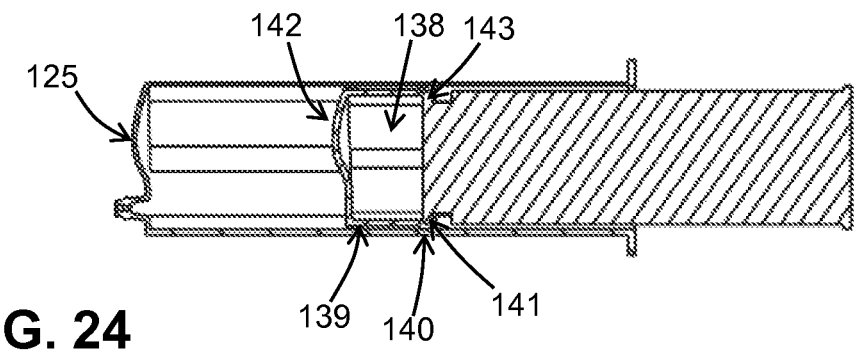
FIG. 23 is a longitudinal cross-section, side view of FIG. 22.
Figure 24:
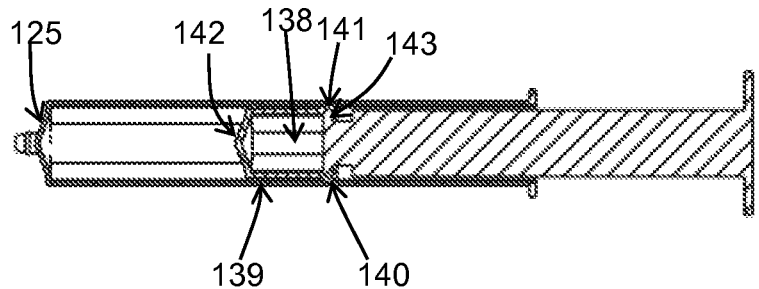
FIG. 24 is an additional longitudinal cross-section, top view of FIG. 22.

FIGS. 23 and 24 are side and top sectional views of syringe 120, respectively. They reveal the fluid tight arrangement of the plunger 122's seal 138 with the inner wall surface 124 of body 121. Seal 138 has two, spaced rings 139 and 140 which sealingly engage sidewall 124 and promote axial travel of the plunger 122. The distal seal wall 142 has the identical configuration as distal wall 123 including central portion 125 to totally evacuate body 121 when plunger 122 is depressed.

FIG. 26 displays an axonometric view of another embodiment 150 utilizing an efficient, circular cylindrical body 155 blending into an elliptical cylinder 154 distally for an aspiration region. This embodiment 150 uses several of the above, previously described features, including plunger 153 and distal wall features 152. The finger placement platforms 165 and 166 are similar in function to detents 67 and 68 in FIGS. 7 and 8 for syringe 40. In this embodiment a circular cylinder 155 is the predominant body configuration with a small, distal, elliptic cylindrical region 154 for aspiration. This provides a maximum volume for the syringe dimensions 150 with an elective aspiration option.

FIGS. 27 and 28 are longitudinal, side and top cross-sections of syringe 150, respectively. The plunger sealing and axial traveling means of seal 156 is identical to FIG. 10. However, the distal configuration 157 mimics the body distal interior 158 of body 151 to provide total evacuation of the syringe barrel when injecting a mendicant. The profiles 159 and 160 of the predominant body regions are the same in both views; however, the elliptical aspirating region is wider in FIG. 26 compared to profile 162 in FIG. 27. This reflects the predominantly circular nature of the body 155 with an elliptical nature of aspirating region 154.

FIGS. 29 and 30 are cross-sectional views of the body 151 in circular cylindrical and elliptic cylindrical regions 155 and 154, respectively. It reveals the uniform, structural wall thickness 163 of the circular region and the varied, yieldable thickness 164 of the elliptical region.

A transition of the syringe body increasing its cross-sectional area and the syringe barrel volume for selective aspiration. The various, above described features can be interchangeable within the various embodiments and utilizing the various embodiments of the subject invention an aspiration and injection procedure can be facilely performed with one hand.

What is claimed is:

1. A syringe barrel comprising:
   a tubular syringe barrel body operable to receive a syringe plunger at a proximal end thereof and a syringe needle at a distal end thereof; and
   sidewalls of said tubular syringe barrel body being at least partially flexible at least along a partial length of said tubular syringe barrel body being generally elliptical in cross-section at least along said partial length and having a sidewall thickness in cross-section that is generally thicker at the ends of the major axis of the elliptical cross-section as compared with a sidewall thickness at the ends of the minor axis of the elliptical cross-section; and
   wherein opposing compression of said tubular syringe barrel body at opposite ends of the major axis of said elliptical cross-section along said partial length of said tubular syringe barrel body serves to operably permit flexing of the generally elliptical cross-section at least partially into a more circular cross-sectional configuration and thus increase a volume within said tubular syringe barrel body and concomitantly serve to create a relative vacuum within said tubular syringe barrel body as compared with an initial configuration of said tubular syringe barrel body prior to application of said compression such that the vacuum serves to draw a test sample of body fluid from a patient into a viewing conical chamber of said tubular syringe barrel body indicating engagement of the syringe needle within the patient's vascular system without premature expulsion of fluid from within said tubular syringe barrel body into the patient prior to confirmation of engagement of the syringe needle within the patient's vascular system.

2. The syringe barrel as defined in claim 1 wherein:
   said distal end of said tubular syringe barrel body terminates in a conical frustum configuration and said conical frustum has an internal fluid passageway in fluid communication with the syringe needle at the distal end of said tubular syringe barrel body, and wherein the viewing conical chamber is within the conical frustum for viewing the test sample drawn into said viewing conical chamber prior to injection of the fluid from said tubular syringe barrel body into the patient.

3. The syringe barrel as defined in claim 1 and further comprising: aspirating ribs at an extension of the major axis of said tubular, barrel body having a generally elliptical cross-section.

4. The syringe barrel as defined in claim 3 and further comprising: opposing finger detents at the distal ends of said aspirating ribs.

5. The syringe barrel as defined in claim 1 and further comprising:
   curved wall sections capping the major axis of said generally elliptical cross-section and curved walls capping the minor axis of said generally elliptical cross-section.

6. The syringe barrel as defined in claim 1 wherein:
   said tubular syringe barrel body comprises the generally elliptical cylinder section axially joined to a truncated elliptic cone section.

* * * * *